United States Patent
Foster et al.

[11] 4,062,353
[45] Dec. 13, 1977

[54] RADIOACTIVE SYRINGE SHIELD HAVING RETENTIVE BUSHING

[75] Inventors: Edward Henry Foster; James M. Reiss, both of Center Moriches, N.Y.

[73] Assignee: Atomic Products Corporation, Center Moriches, N.Y.

[21] Appl. No.: 703,515

[22] Filed: July 8, 1976

[51] Int. Cl.[2] .............................................. A61B 6/00
[52] U.S. Cl. ..................... 128/1.1; 128/2 A; 128/215; 250/506
[58] Field of Search ............ 128/1.1, 2 A, 215, 218 R, 128/218 P, 218 PA; 250/506, 512, 513, 515, 108 R

[56] References Cited
U.S. PATENT DOCUMENTS

| | | | |
|---|---|---|---|
| 3,596,659 | 8/1971 | Glasser | 128/215 |
| 3,973,554 | 8/1976 | Tipton | 128/1.1 |

*Primary Examiner*—John D. Yasko
*Attorney, Agent, or Firm*—Charles E. Temko

[57] ABSTRACT

A radioactive syringe shield for protecting a user from radiation emanating from a radioactive material disposed within an enclosed syringe, characterized in the provision of a removable arcuately shaped bushing positionable in the bore of the shield for decreasing the effective diameter thereof to support a syringe barrel against a single set screw. The bushing is inserted with the syringe barrel into an oversized bore in the shield permitting passage of the needle of the syringe with an intact needle cover, thereby maintaining sterility of the needle.

3 Claims, 7 Drawing Figures

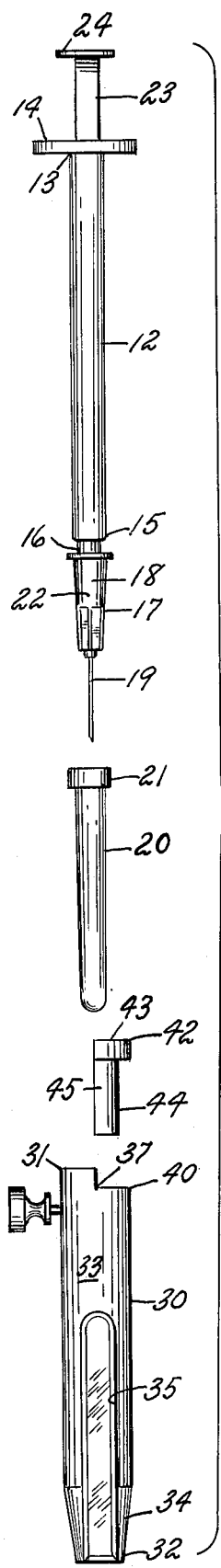
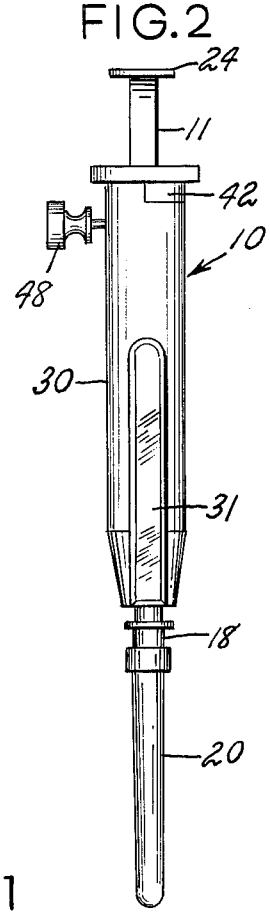
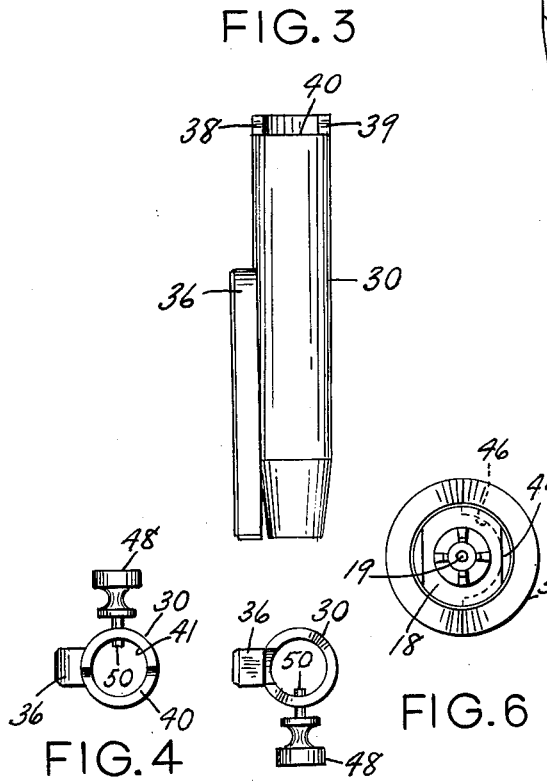
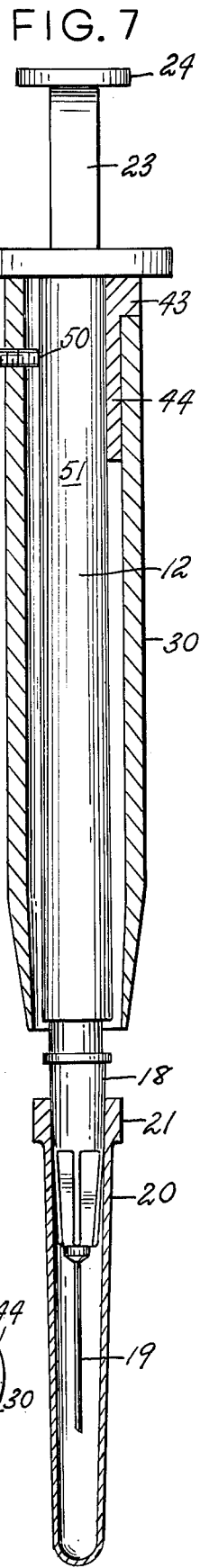

RADIOACTIVE SYRINGE SHIELD HAVING RETENTIVE BUSHING

BACKGROUND OF THE INVENTION

It is well known in the art to provide removable shielding adapted to engage a hypodermic syringe in such a manner as to surround the barrel thereof and thereby shield a user from the radioactive contents of the syringe. Most such devices include a bayonet-type locking means at an upper or proximal end thereof adapted to engage the outwardly projecting syringe flanges formed integrally with the barrel and normally contacted by the fingers of the user during the discharge of the contents of the syringe. Prior art syringe shields also include the use of lead, tungsten or other shielding materials which cover the major portion of the length of the syringe barrel, leaving an exposed tip to which the usual needle and cover therefor are attached.

When using relatively small, i.e. one cc capacity, syringes, the barrel of the syringe is usually not locked into position by flanges, but instead is secured by a single set screw penetrating the shield and bearing against the barrel of the syringe which is of an outer diameter substantially corresponding to that of the bore in the shield. Unfortunately, the diameter of the needle cover is usually greater than that of the barrel, necessitating the removal of the cover from its protective position enclosing the needle each time the syringe is removed from the shield, as, for example, when the contents of a loaded syringe are calibrated for radioactivity. This requirement leaves the needle exposed and possibly contaminated.

SUMMARY OF THE INVENTION

Briefly stated, the invention contemplates the provision of an improved syringe shield of the type disclosed, particularly adapted for use with syringes of relatively small capacity, in which the insertion and removal of the syringe within the bore of the shield may be accomplished without the necessity of removing the needle cover. To this end, the shield is formed to include a bore of diameter sufficient to pass the needle cover, and a removable, arcuately shaped, sleeve having an outer surface of radius corresponding to that of the bore of the shield and an inner surface of radius corresponding to that of the outer surface of the syringe barrel to form a bushing aligning the syringe barrel with the bore of the shield, and distributing stress caused by engagement of the barrel with the said screw over a substantial area.

BRIEF DESCRIPTION OF THE DRAWING

In the drawing, to which reference will be made in the specification, similar reference characters have been employed to designate corresponding parts throughout the several views.

FIG. 1 is an exploded view in elevation of a combination syringe and shield therefor embodying the disclosed invention.

FIG. 2 is an assembled side elevational view thereof.

FIG. 3 is a side elevational view of the shield.

FIG. 4 is a top plan view of the shield.

FIG. 5 is a bottom plan view of the shield.

FIG. 6 is a bottom plan view of the shield with a syringe in position.

FIG. 7 is an enlarged fragmentary longitudinal central sectional view as seen from the plane 2—2 in FIG. 6.

DETAILED DESCRIPTION OF THE DISCLOSED EMBODIMENT

In accordance with the invention, the device, generally indicated by reference character 10, is illustrated in the drawings in operative relation with a known hypodermic syringe 11 of relatively small capacity. The syringe is formed principally of synthetic resinous materials, and includes a barrel element 12 including a proximal end 13 having a finger-engaging flange 14 thereon as well as a distal end 15 forming a seat 16 for a detachable needle element 17. The needle 17 includes a base member 18 and a hollow needle member 19, the base 18 engaging a protective cover 20 having a finger-engaging flange 21, and selectively engaging a tapered surface 22 on the member 18. Penetrating the barrel element 12 is a manually operated plunger 23 having a thumb-engaging tip 24.

The device 10 includes a main barrel member 30 of tungsten, tantalum, or similar radioactive shielding material. It is bounded by a proximal end 31, a distal end 32, an outer cylindrical surface 33 and an outer tapered surface 34. An elongated slot 35 is covered by a lead glass window 36 to permit volumetric calibration of the syringe 11.

Adjacent the proximal end 31 is an arcuately shaped notch 37 bounded by vertical surfaces 38 and 39 and a horizontal surface 40. A cylindrical through bore 41 is of a diameter sufficiently large to permit passage of the widest part of the cover 20.

Selectively positioned within the bore 41 is an arcuately shaped sleeve 42 forming a bushing. The sleeve includes a recess engaging portion 43 of configuration conforming to that of the notch 37, and an elongated portion 44 having an outer surface 45, the radial curvature of which corresponds to that of the bore 41. An inner cylindrical surface 46 corresponds in curvature to that of the outer surface of the barrel element 12. Engagement of the portion 43 within the notch 37 alines the portion 44 to intersect with the axis of an oppositely disposed threaded bore 47 engaging a set screw 48 having a threaded shank 49, the inner end 50 of which bears upon the outer surface 51 of the barrel 12, as best seen in FIG. 7 in the drawing.

From a consideration of FIG. 1, it will be observed that the assembly of the syringe with the shield and attached needle cover requires the loosening of the set screw means to permit passage of the needle cover and the barrel of the syringe with abutted sleeve. When the set screw has been retracted to clear the bore in the shield, the components may be rapidly positioned as shown in FIG. 7, prior to tightening of the set screw means. It will be observed that the reaction of the sleeve and set screw tends not only to distribute the stresses applied to the barrel of the syringe over a substantial area, but to coaxially aline the syringe barrel and the sleeve whereby the manual manipulation of the assembled combination is facilitated. Thus, when a syringe is loaded, and allowed to await usage, the necessary radioactive calibrating procedure can be performed conveniently, and the shield replaced without the necessity of exposing the needle to contamination.

I wish it to be understood that I do not consider the invention limited to the precise details of structure shown and set forth in this specification, for obvious modifications will occur to those skilled in the art to which the invention pertains.

I claim:

1. In a combination hypodermic syringe and removable radioactive shield therefor, the improvement comprising: said syringe having a main barrel element of given outer diameter, a needle element on a distal end thereof, and a needle cover enclosing said needle element and having an outer diameter greater than that of said barrel element; said shield including a generally tubular body defining an axially disposed through bore therein of diameter at least equal to the diameter of said needle cover, set screw means penetrating said tubular body and having an inner end thereof adapted to contact an outer surface of said main body of said syringe; and an arcuately shaped sleeve having an outer surface of radius corresponding to that of said through bore, and an inner surface of radius corresponding to said given diameter of said main barrel of said syringe, said sleeve being selectively positioned between said through bore and said main barrel element to lie at least partially along the axis of said set screw means to position said main barrel coaxially relative to said through bore, and permit selective withdrawal of said syringe with attached needle cover through said last mentioned bore.

2. Structure in accordance with claim 1, further characterized in said tubular body having a notch therein at a proximal end thereof, said sleeve having a correspondingly-shaped enlargement selectively seated within said notch to predetermine the position of said sleeve relative to said tubular body.

3. Structure in accordance with claim 1, further characterized in said sleeve subtending an arc of substantially 180°.

* * * * *